US008663108B2

(12) United States Patent
O'Kane

(10) Patent No.: US 8,663,108 B2
(45) Date of Patent: Mar. 4, 2014

(54) METHOD AND SYSTEM FOR RAPIDLY AND PASSIVELY IDENTIFYING CHANGES IN NUMBER OF OPEN PORES IN THE SKIN OF AN INDIVIDUAL

(75) Inventor: Barbara L. O'Kane, Franconia, VA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 369 days.

(21) Appl. No.: 12/570,450

(22) Filed: Sep. 30, 2009

(65) Prior Publication Data

US 2010/0191077 A1    Jul. 29, 2010

Related U.S. Application Data

(60) Provisional application No. 61/147,835, filed on Jan. 28, 2009.

(51) Int. Cl.
*A61B 5/00* (2006.01)
(52) U.S. Cl.
USPC .......................................... 600/306; 600/307
(58) Field of Classification Search
USPC ................................................ 600/306, 307
See application file for complete search history.

(56) References Cited

U.S. PATENT DOCUMENTS

| | | | |
|---|---|---|---|
| 4,931,934 A | 6/1990 | Snyder | |
| 5,507,291 A | 4/1996 | Stirbl et al. | |
| 6,585,521 B1 | 7/2003 | Obrador | |
| 6,656,116 B2 | 12/2003 | Kim et al. | |
| 6,837,615 B2 | 1/2005 | Newman | |
| 6,852,086 B2 | 2/2005 | Atlas et al. | |
| 6,854,879 B2 | 2/2005 | Pavlidis | |
| 6,996,256 B2 | 2/2006 | Pavlidis | |
| 7,027,621 B1 | 4/2006 | Prokovski | |
| 7,111,980 B2 | 9/2006 | Pavlidis et al. | |
| 7,138,905 B2 * | 11/2006 | Pavlidis et al. | 340/5.81 |
| 2003/0120140 A1 | 6/2003 | Bango, Jr. | |
| 2008/0194928 A1 * | 8/2008 | Bandic et al. | 600/306 |
| 2010/0191124 A1 * | 7/2010 | Prokoski | 600/473 |

OTHER PUBLICATIONS

Ring, Progress in the Measurement of Human Body Temperature, Jul./Aug. 1998, IEEE Engineering in Medicine and Biology, pp. 19-24.*
Freedman et al., The relationship of sweat gland count to electrodermal activity, Mar. 1994, Psychophysiology, vol. 31 Issue 2, p. 196-200.*
Barbara L. O'Kane and Cary D. Balaban, Dynamic High Resolution Thermograms of Human Skin, InfraMation 2006 Proceedings.
Barbara L. O'Kane, Philip Sandick, Todd Shaw and Mike Cook, Dynamics of Human Thermal Signatures, Inframation 2004.
Lauren W. Freedman, Angela Scarpa Scerbo, Michael E. Dawson, Adrian Raine, William O. McClure and Peter H. Venables, The Relationship of Sweat Gland Count to Electrodermal Activity, Psychology, vol. 31, pp. 196-200 (1994).

* cited by examiner

*Primary Examiner* — Michael Kahelin
*Assistant Examiner* — Tho Tran
(74) *Attorney, Agent, or Firm* — Richard Kim

(57) ABSTRACT

In one aspect, there is disclosed a system and method for rapidly and passively identifying changes in the number of open pores in the skin of an individual in response to a stimulus without contacting the individual. This is accomplished by using a thermal camera that is sensitive in the mid-wave or long-wave infrared (3-5 or 8-14 μmeters) to observe and/or count the number of skin pores opening in response to questions being asked of the individual.

18 Claims, 7 Drawing Sheets

METHOD AND SYSTEM FOR RAPIDLY AND PASSIVELY IDENTIFYING CHANGES IN NUMBER OF OPEN PORES IN THE SKIN OF AN INDIVIDUAL

CROSS-REFERENCE TO RELATED APPLICATIONS

This application claims the benefit of Provisional Application No. 61/147,835, filed Jan. 28, 2009.

GOVERNMENT INTEREST

The invention described herein may be manufactured, used, sold and/or licensed by or for the United States Government.

FIELD OF THE INVENTION

The invention relates to a method and system for rapidly and passively identifying the changes in the opening of pores in the skin on the face, hand, or fingers of an individual exposed to different external stimuli without physically making contact with the individual.

BACKGROUND OF THE INVENTION

An effort was made to develop a system which could utilize the principles of a polygraph, or "lie detector", but would be remote and not require physical contact with the person to be tested. A key component of a polygraph is the measuring of the Galvanic Skin Response (GSR), also termed Electro-Dermal Activity (EDA) or Electro-Dermal Response (EDR), or Sympathetic Skin Response (SSR). For this application, the term EDR will be used to refer to this response. In a polygraph, the EDR is measured by placing an electrode on each of two finger tips such that the measurements provide an instantaneous measurement of skin conductance or its inverse, skin resistance. During a typical polygraph examination, the subject is instructed to remain perfectly still and answer "yes" or "no" to a series of planned and previously discussed questions. Changes in skin conductance/resistance immediately following relevant questions are used to determine the stress of deception during such polygraph examinations.

It is well known in the polygraph literature that if a small amount of electrical current is passed through the body, the electrical conductance/resistance of the skin can be measured. See Matte, James Allan, "Forensic Psychology Using the Polygraph," J.A.M. Publications, Williamsville, N.Y., 1996, One of the primary functions of the polygraph is to measure the physiological activity that accompanies physiological stress reactions to telling a lie or of fear of being caught in a lie. See Vrij, Aldert, "Detecting Lies and Deceit," John Wiley: West Sussex, 2008, p. 294. During a deceptive response, the resistance of the skin decreases, and conversely the conductance rises. It has been speculated that opening of the skin pores is related to an increased conductance of the skin. See Freedman, L. S., et al., "The Relationship of Sweat Gland Count to Electrodermal Activity," Psychophysiology, 1994, 31(2): 196-200 and Juniper, K, Blanton, D. E. & Dykman, R. A., "Palmar Skin Resistance and Sweat-gland counts in Drug and Non-drug states, Psychophysiology, 4, 231-243 (1967). In each of these cases, however, the number of skin pores on the hand was related to the EDR on the finger tips in one instant in time. A sweat gland count was accomplished by painting the finger or palm with, for example, a solution of iodine and alcohol and making an imprint or counting the black sweat pores on the palm as showing sweat pores.

Other researchers have reported that the sweat response is a sensitive indicator of sympathetic activation during mental arithmetic and distressing films. See D. Yamashiro et al., "Sympathetic Skin Response and Emotional Changes of Visual Stimuli, No To Hattatsui. 2004 September: 36(5): 372-7 [Article in Japanese, only abstract translated]. One useful measure of palmar sodometer (perspiration) activity has been a Palmar Sweat Index (PSI), defined as a number of spots of sweat in a 4 $mm^2$ skin region. T. Kohler et al., Z. Exp. Angew Psychol., 36(1): 89-100 (1989). The PSI was measured from plastic casts of the skin taken at 2.5 minute intervals. However, there was no way to observe the number of open pores in real time until the present invention.

The "fight or flight" reflex is a universal physiological response to threatening stimuli. See Cannon, Walter B., "Bodily Changes in Pain, Hunger, Fear and Rage: An Account of Recent Researches into the Function of Emotional Excitement," Appleton, N.Y., 1915. The reflex occurs through the activation of the sympathetic nervous system and is accompanied by sudden and significant changes in the physiology of the body. Heart and breathing rate increase. Sweat glands prepare to cool the body. Pupils of the eyes dilate presumably to bring in more light to better see the threatening stimulus. This "fight or flight" reflex underlies the most significant component of the polygraph, the change in skin conductance that is associated with the threat of being caught in a lie or being discovered as the perpetrator of a crime and suffering the penalty of such discovery. This reflex is used in the polygraph to detect that a person is at the present moment under observation responding to a question that relates to involvement in a crime and lying during a polygraph examination.

All polygraph techniques essentially attempt to show a difference between responses to questions that are relevant to the particular crime in comparison with those that are not. A person guilty of a crime is presumably going to respond to a greater extent to relevant questions than an innocent person would or than to questions that are not relevant to a crime for which he could suffer punishment (jeopardy). There are several major techniques or formats for structuring the questions during a polygraph examination. These techniques fall into the following categories:

Control Questions Testing: Questions that would be non-threatening to an innocent person but threatening to a guilty person with respect to the particulars of the crime committed.

Relevant-Irrelevant: Questions that have a control lie question to compare with the particular relevant question(s) related to the crime.

Guilty Knowledge The suspect is asked several questions about the crime that includes details that only the crime investigators and the criminal would know about. If the suspect consistently shows the strongest emotional reaction to questions containing correct details, such responses would suggest that he is the criminal and possesses knowledge that only the criminal would have.

Peak of Tension Test: The Peak of Tension Test is similar to the Guilty Knowledge Test except that the details are asked in a certain order and the suspect can expect the detail to come in the question. As the interviewer reaches the detail of interest the person will tend to increase in conductance response.

The "Timely Reaction Rule" provides guidelines for determining whether a reaction is related in time to a particular question. Specifically, it states that the response (change in conductance) must occur following the first word of the question or if the response starts within five seconds of the answer being given.

Lie detectors or polygraphs have been used for years to determine the truthfulness of a person's answers and as a result, the trustworthiness for employment. The polygraph requires an expert to give the test and interpret the results. It also requires that a person be willing to be tested and be connected to various electronic devices.

There are many situations within law enforcement, military, and intelligence scenarios in which it is highly advantageous and sought-after to determine whether a person is concealing knowledge or information about a crime, a terrorist act, or other such important event and its perpetrators. This determination can be improved when the person's physiological responses can be observed without physical contact with the subject. In a battlefield scenario, unlike a criminal event in law enforcement, the goal is not strictly to get a confession of guilt from a detainee or to determine whether the detainee has committed an actual act of terrorism or counterinsurgency. More importantly, it is often to find the network, the bomb maker, or other information that may be known to the subject. Similarly, when an event takes place, there may be many innocent civilians in the area who have information they are concealing to keep themselves or loved ones safe.

Within the United States, ever since the tragic intentional airplane crashes on Sep. 11, 2001, there has been an increased interest in identifying individuals flying within and into the United States, who may be dangerous and could cause serious harm to a significant number of American citizens and residents. Although individuals coming into the United States from a foreign country are required to have and show a passport, this does not indicate if they may be dangerous. However, if they are on a "no-fly" list, they may be subject to special procedures prior to being permitted to board a plane.

Persons boarding a plane usually have to go through a screening procedure where they are viewed by a Transportation Security Administration official and their carry-on luggage is scanned by a metal detector. People coming in from outside the United States go through customs where their luggage may be inspected and they may be asked a few general questions. If these individuals were concealing information about any imminent violent intentions with respect to the United States, it would be advantageous to be able to interview them effectively about their intentions.

Various systems have been developed to measure the emotional response of individuals remotely. One of these was by Ioannis Pavlidis who used a thermal camera to measure the change of blood flow in the subject's face, and particularly in the periorbital region and forehead. He obtained patents on this technology, including U.S. Pat. Nos. 6,854,879, 6,996,256, 7,111,980 and 7,138,905. These systems all require transforming the thermal image data to blood flow data.

John Newman also recognized that a person's skin temperature will increase because of anxiety and developed a system described in U.S. Pat. No. 6,837,615, which measures the differences in skin temperature in the face and neck.

Finally, Francine Prokoski disclosed in U.S. Pat. No. 7,027,621 an embodiment of an invention for screening interviewees and applicants to detect possible deception using a thermal camera focused on the face of the interviewee or applicant to detect and monitor thermal variations.

SUMMARY OF THE INVENTION

The present invention is directed to a method for a rapid and passive identification of changes in the number of open sweat pores in the skin of an individual, comprising disposing a thermal camera at a predetermined location; focusing the thermal camera on at least a portion of a predetermined skin surface of the individual so as to provide a thermal image without contacting the individual; displaying the thermal image to enable real time viewing of the pores on the portion of the predetermined skin surface; interviewing the individual presenting a stimulus; and detecting the opening of pores on the portion of the predetermined skin surface in response to the stimulus.

In one preferred embodiment of the method, the thermal camera is disposed at a predetermined location so that the thermal camera is hidden from the view of the individual. In another embodiment, the predetermined skin surface is a portion of the face.

Preferably the stimulus is selected from a group consisting of one or more questions, pictures, video or audio recordings to be presented to the individual.

In an alternative embodiment, the stimulus is a series of questions being asked the individual.

In one alternative embodiment, the method further comprises providing an automatic pore counting means. Furthermore, the thermal camera is a FLIR midrange camera.

The method of the present invention also comprises providing a computer with an electronic display and a storage medium and coupling the thermal camera to the computer. The method also comprises displaying the thermal image on the computer's electronic display.

Preferably, the computer can be a laptop.

The method further comprises providing a temperature and humidity sensing device to enable monitoring of the temperature and humidity in the vicinity of the individual and coupling the sensing device to the computer. Also a microphone can be provided to enable recording the audio of the interview and coupling the microphone to the computer.

The method also comprises providing a color video camera to enable recording the video of the interview and coupling the color video camera to the computer.

According to another preferred embodiment, the method comprises providing an application program code disposed on the storage medium of the computer. The application program code is operable to enable recording on the storage medium of the thermal images, the video and the audio of the interview.

In an alternative embodiment, the application program code is operable to enable selectively providing an event marker at a selected location of the recording to identify the occurrence of the opening of the pores.

In another preferred embodiment, the application program code is operable to enable selectively configuring the operation of the thermal camera.

In yet another preferred embodiment, the application program code is operable to enable selectively configuring the operation of the video camera.

In still another embodiment, the application program code is operable to enable selectively configuring the operation of the microphone.

The present invention is also directed to a method for a rapid and passive determination of whether an individual is withholding information comprising providing a thermal camera to measure the number of open sweat pores in the face of the individual; requesting the individual to supply information; and observing the increase in the number of open pores in the skin of that individual in response to the request for information.

In addition, the present invention is also directed to a system for a rapid and passive identification of the changes in the number of open sweat pores in the skin of an individual in response to a stimulus. The system can comprise a thermal camera as well as a means for focusing the thermal camera on at least a portion of a predetermined skin surface of the individual so as to provide a thermal image without contacting the individual. The system further comprises a display to show the thermal image to enable real time viewing of the opening of pores on the portion of the predetermined skin surface. Also, the system comprises a means for identifying the opening of pores on the portion of the predetermined skin surface as a response of the individual exposed to a stimulus.

According to one embodiment of the invention, the stimulus is one or more questions presented to the individual.

The system in a preferred embodiment further comprises a computer. The computer can have an electronic display and a storage medium. Means for coupling the thermal camera to the computer can also be provided. In one preferred embodiment the computer is a laptop.

The system can also comprise a temperature and humidity sensing device to enable monitoring of the temperature and humidity in the vicinity of the person. In addition, the system can include a microphone to enable recording the audio of the interview and means for coupling the microphone to the computer. In another embodiment, a color video camera is provided to enable recording the video of the interview and means is provided for coupling the color video camera to the computer. The thermal camera can be a FLIR midwave camera.

According to another preferred embodiment, the system comprises providing an application program code disposed on the storage medium of the computer. The application program code is operable to enable recording on the storage medium of the thermal images, the video and the audio of the interview.

In an alternative embodiment, the application program code is operable to enable selectively providing an event marker at a selected location of the recording to identify the occurrence of the opening of the pores.

In another preferred embodiment, the application program code is operable to enable selectively configuring the operation of the thermal camera.

In yet another preferred embodiment, the application program code is operable to enable selectively configuring the operation of the video camera.

In still another embodiment, the application program code is operable to enable selectively configuring the operation of the microphone.

BRIEF DESCRIPTION OF THE DRAWINGS

The following and other objects, aspects and advantages will be better understood from the following detailed description of preferred embodiments of the invention with reference to the drawings, in which.

DETAILED DESCRIPTION OF THE PREFERRED EMBODIMENTS

Figure 1:
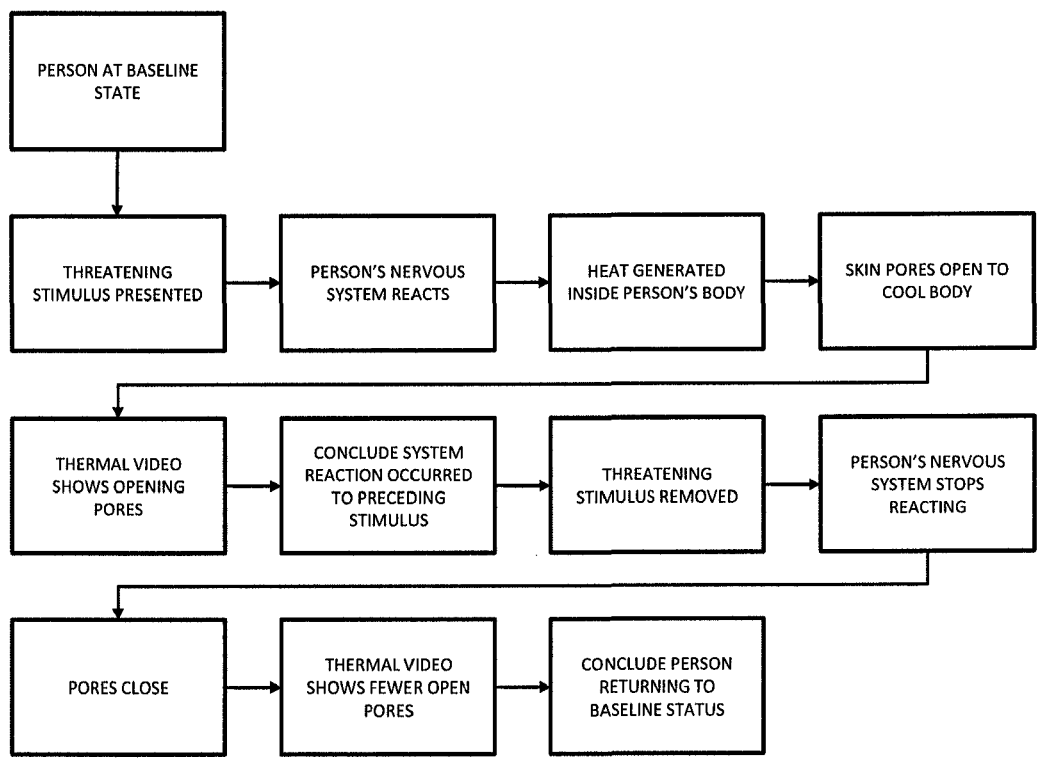
FIG. 1 illustrates a flow chart of the operation of the invention.

The present invention includes a sensing device such as a thermal camera with sufficient resolution to discriminate open sweat pores. Sweat pores are nominally 0.1 mm in diameter. One example of a thermal camera used in the invention provides a resolution of at least 0.3 mm of skin per pixel and allows the visualization and counting of open pores in real time at nominally 10 frames per second. The number of open pores that can be observed by means of a thermal camera or imager directly relates to the conductance changes in the skin. The present invention capitalizes on the uses of the electrical response of the skin by observing the change in the number of pores as they open and close in response to the subject's "fight or flight" reflexes. Since the number of pores is related to the EDR, much of the research literature and usefulness of EDR can be applied to this invention. The pores in this invention may easily be visualized on the face or on the fingertips, including the thumb. Both relate to the EDR.

This invention is designed to observe the opening of the sweat pores that is related to the formerly used EDR of a person when that person experiences the "fight or flight" reaction due to any of a number of causes:
  concealing a secret intention and afraid of being found out;
  experiencing an emotional reaction to a stimulus (such as the mention of a topic that causes fear);
  hearing or seeing a stimulus that evokes an emotional reaction (the name of an enemy, seeing a picture of a snake); and
  observing a traumatic scenario.

This invention utilizes the fact that a human being emits considerable thermal energy. The reasons for this are many. Specifically, a human's core temperature is approximately 98.6° F. (37° C.). The average of skin temperature on the face has been found to be approximately 32° C. Thermal cameras in both midwave (3-5 μmeters wavelength) and longwave (8-14 μmeters wavelength) are able to measure and display this thermal energy due to the large number of photons emitted from the body in those wavebands.

In contrast to other inventions using thermal imagery to reveal deception, the present invention uses a particular feature that is observable in the thermal video, namely the number and spatial location of open pores on the face. The change in the number of open pores and the number of pores that remain open or open and close relatively slowly, and the specific locations on the face of the opening and closing pores are each important to this invention.

The thermal camera is used to see what can be called the "O'Kane Effect." This phenomenon is as follows: a person before any stimulus is applied or stressful question asked has a baseline number of pores. Immediately following any threatening stimulus is perceived, there is a resulting "rush" of adrenaline related to the "fight or flight" reflex. This stimulus response of adrenaline causes a heating of the internal body through the nervous system activation and this, in turn, causes the pores on the skin to open to begin the process of cooling the body back to its normal temperature. The "O'Kane Effect" is the appearance of the pores opening as observed in thermal imagery, right after the initiation of and for the duration of the "fight or flight" response. If the sense of threat continues, the pores may remain open or their numbers continue to increase and when the threat passes, the pores will close. The pores begin to open within about a half second of the stimulus and then close as the person relaxes. The "O'Kane Effect" is also directed to associating the location of the opening of the pores in response to various stimuli.

The thermal camera of the invention is one which is sensitive to radiation in the electromagnetic spectrum including wavelengths between approximately 3-5 or 8-14 μmeters. It should have 100+/−10 linear pixels by 100+/−10 linear pixels per inch of the subject's face and temporal sensitivity of at least 4 frames per second (4 Hz). The video from a thermal imager is used so that what is being visualized according to this invention are the relatively cool spots, centered over the pores of the skin, each of which is approximately 1 mm in diameter, in their contrast with the relatively warm part of the skin that is not the open pores. The apparent temperature difference, taking into account that some of this difference may be due to differences in emissivity between the pore contents and the skin, is between 0.5 and 2° C. This opening and closing of the pores is highly correlated with the EDR of the skin, which is the key component of the polygraph test. The significant correlation between the number of open pores on the finger and the EDR sampled at 25 Hz has been verified by experiments with hundreds of test participants. These experiments were conducted and analyzed by the inventor. In addition, the relationship between the number of open pores on the forehead and the EDR on the forehead has been substantiated in testing. A significant correlation between the number of open pores on the face and the EDR measured on the fingertip has also been observed in various experiments and demonstrations.

Three different thermal cameras were used in the demonstration of the invention. All three cameras were developed by CEDIP Infrared Systems. The three camera models used were the Jade, Emerald and Silver. Each of the systems used were midwave systems 3-5 μm with either mercury cadmium telluride cooled camera (MCT) or indium antimonide (InSb) focal planes. The Jade sensor had a 320×240 pixel focal plane array while both Emerald and Silver had 512×640 pixel focal plane arrays. Both the Emerald and the Silver were the primary thermal cameras used in the demonstration of the invention. Higher and lower resolution/sensitivity cameras were also used to demonstrate the capability of observing pores opening and closing. This included a high resolution (1024× 1024) midwave sensor, the FLIR SC8000, as well as lower resolution and lower sensitivity microbolometer cameras such as the FLIR Systems SC1000, SC2000 and SC3000. With the appropriate optics, pores could be observed on the face using the previously listed sensors at distances ranging from 1 cm to 4 m optimally from the individual's face. Pores could be observed at further distances given the appropriate optics and sensor characteristics. It was noted that the pores opened and closed during visual stimuli of various kinds during an interview of the interview. In order to observe the pores, it is preferable to optimize the resolution of the camera by using a lens which focuses at such a distance that nearly all of the detector pixels are focused on the face, not on the background or the hair, both of which are irrelevant to the invention. If the rectangular detector array is viewed in the "portrait" format, for example, 512×640, with most pixels in the vertical direction, maximum use is made of the detector pixels since the aspect ratio of the face is not landscape (as most thermal cameras are designed) but more like a portrait format.

One of the key functions of the skin is thermoregulation that keeps the core temperature at a stable level. Any heat generated must be released and is normally done so in humans through the sweating process. Of interest in this invention is the skin response to heat generated by the nervous system action. It is believed that the opening of the pores and presumably changes in the sweat ducts below the skin contributes to the changes observed in EDR used in the polygraph. The changes in the sweat ducts are a response to the increased heat generated in the body by the nervous system discharge that the skin immediately attempts to release through the opening of pores on the skin. Beneath these pores are ducts that have fluid and this fluid can rise to the surface of the skin where it can be evaporated to reduce the heat. The reason for the correlation between the EDR and the number of open pores on the face and finger, is that the increase in skin resistance (or conversely the decrease in resistance) that is used as the EDR is due to the fact that open pores provide less resistance than intact skin.

A desirable spatial resolution for the best visualization of the pores is to have at least 7,000 detector pixels per square inch of skin on the subject. This can be accomplished with the appropriate camera resolution, distance from the subject, and lens. With the 512×640 CEDIP Emerald, the preferred distances between the front plane of the camera lens and the subject's face is approximately 1.2 m with a 50 mm lens, 2.5 m with a 100 mm lens, and 5 m with a 200 mm lens for optimal pixels on target. It should be noted that diffraction effects and other optical limitations may impact the ability to identify open pores at increasing distances.

In order to ensure that the face stays generally in the center of the field of view, a software program is used that tracks the key features of the face and moves the mask that covers the parts of the face on which the pores are to be counted (the forehead, cheeks, nose, mouth area and chin. Creating a mask has the dual purpose of allowing the real-time pore counting to occur on less pixels of the face, saving bandwidth of the computer, as well as reducing false pixels being registered on the hair or around the edges of the subject's spectacles. This tracking of the face can also be used to pan or tilt the camera should the person's face begin to move outside of the field of view of the camera. In order to use this program, a programmable pan/tilt (also known as a gimbal) can be used. Such pan/tilts are produced by many companies.

The invention may include a standard color video camera, an electronic display or screen and a desktop or laptop computer for camera control and data storage/analysis. This equipment may be used with the thermal camera to focus on the individual's face, and display and/or record the thermal and visible video data of the face as the individual is being subjected to questioning or interviews. The particular video camera used was an Imaging Source FireWire ¼" Sony progressive scan CCD zoom unit with a resolution of 640×480 pixels. This was a FireWire plug and play device. The cameras can be positioned on a pan/tilt unit positioned on top of an adjustable tripod or stand so that the cameras can be appropriately positioned by an operator with respect to the individual being tested. This tripod and pan-tilt setup on which the cameras are mounted can be remotely positioned to properly visualize the subject's face by means of a remote control, such as a joystick or keyboard/mouse combination.

The video camera can be connected to a desktop or laptop computer. The invention was operated with a Panasonic Toughbook 52 computer using 32 bit windows XP Professional SP3. It is desirable to have a temperature and humidity monitor or sensor connected to the computer because it is helpful to know the temperature and humidity when the testing is being conducted. This is because the pore activity can be impacted by environmental variations such as these. The sensor used to demonstrate the invention was a Temperature and Humidity Monitor (THUM). The resolution of the sensor was +/−0.72 F at 41-104 F and 2% RH at 10%-90% RH. The range of the sensor was −40° F. to 125° F. and 0% to 100% RH. A microphone may also be connected to the computer which the interrogator may use to record the questions and answers during the interview for later analysis. In the practice of the invention, an Audio-Techinca ATR55 cardiod condenser shotgun microphone was used. The computer may also have an external hard drive or other external storage medium to record the questions, answers, and the thermal and visual videos of the face of the individual. In some instances, it may be desirable to locate the cameras outside the sight of the individual being tested.

It is expected that during a recording of a test, a person will make notes regarding the responses and reaction to the questions being asked. This person should not be the interviewer. In addition, the operator could add event markers during the recording, which is not limited to visualization changes in pore activity. Every time an event is added, information can be typed into the notes field.

It is preferable if the individual is comfortably warm (room temperature 72-78° F.) so that any added heat load imposed by a nervous reaction will result in the body attempting to cool itself through the opening of the skin pores. Therefore, the invention preferably can be used in an environment that is approximately 75° F. although this is not a requirement. If the individual has just performed physical exercise that has caused him or her to begin sweating, or if the subject is in a warm environment, above 75° F., then any body motion or exertion may introduce the need for thermoregulation and pores may subsequently open. The opening of the pores can be distinguished from those caused by a nervous reaction through the time delay with the relevant stimuli. Other cues, such as gestures, nervous movement of the arms and legs, and excessive personal grooming motion, can be observed as additional cues to the stress response of the individual.

Referring to FIG. 1, the flow chart shows basic process steps of the invention, including providing a thermal video device for observing the temperature pattern on the face of a person of interest relating to pore activity, exposing that person to a stimulus to elicit a response, observing any changes in the pore activity as a result of the stimulus for up to 30 seconds following initiation of the stimulus and observing the change in pore activity as measured by pore densities on the face. Pore activity refers to the opening and closing of pores on the skin of the face that is observable through the output of a thermal video device.

Figure 2:
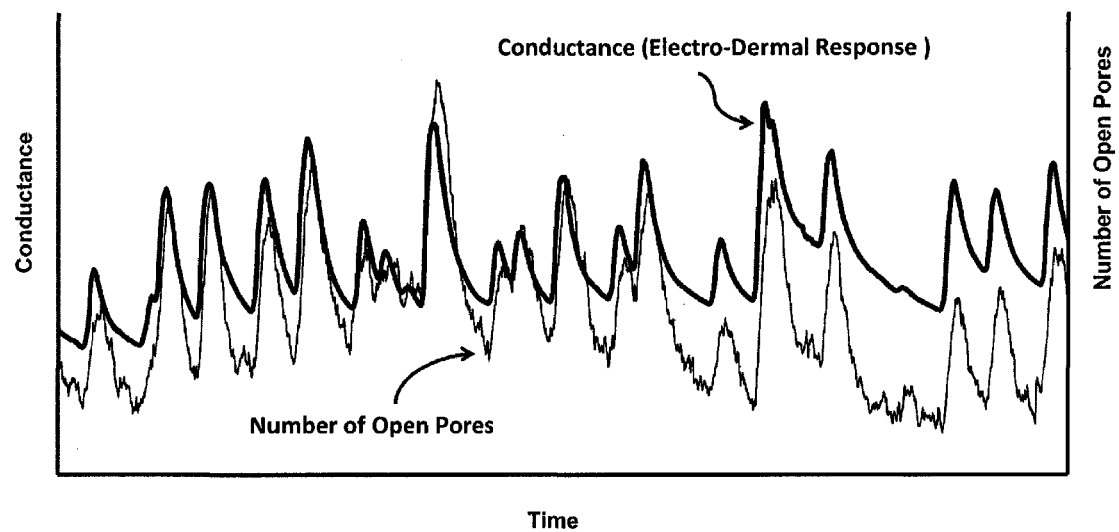
FIG. 2 is a graph over time of the relative number of open pores and changes in the conductance of the skin.

FIG. 2 shows a graph having two curves from an individual subject who is watching a film clip for approximately two minutes. The heavier line is the conductance as measured by contact electrodes on the forehead. The lighter line is the count of open pores visualized in the thermal video for the same time period. This graph shows the high points in pore count and in electrical conductance occurring at the same time for all intents and purposes. The Pearson correlation between the two curves is 0.69, a correlation that is significant with p<0.001. This was the validation of the concept of the number of open pores being a correlate to the conductance value obtained traditionally with electrodes.

The open pores can be observed by a person viewing a monitor display of the thermal imagery of the face or can be counted by an automatic counting algorithm. The open pores in this figure have a temperature difference of 0.1 to 2.0 degrees C.

Figure 3:
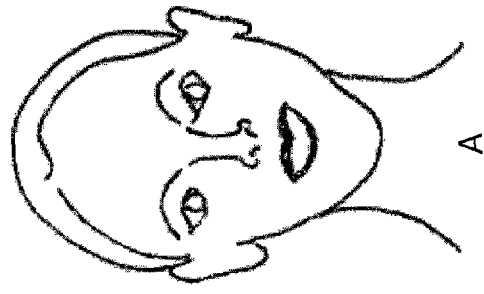
FIG. 3 illustrates the nominal patterns of open pores on six faces showing five different emotions and one with no emotion.
Figure 3:
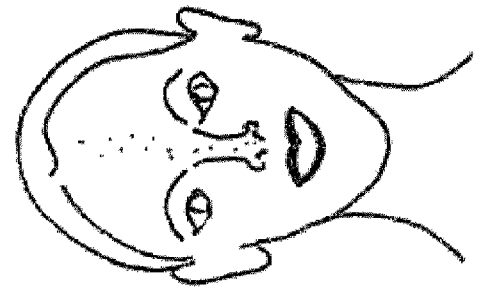
Figure 3:
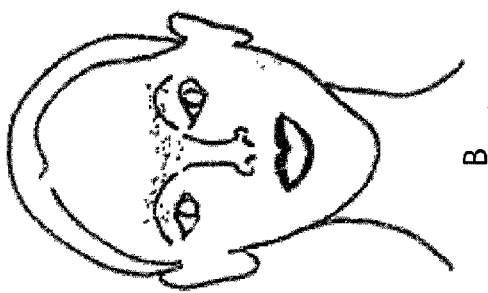
Figure 3:
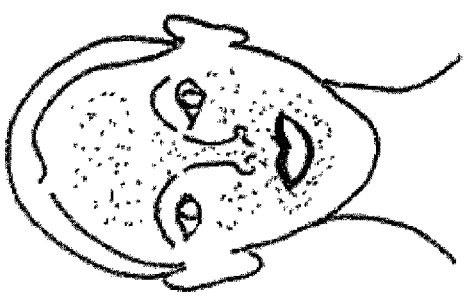
Figure 3:
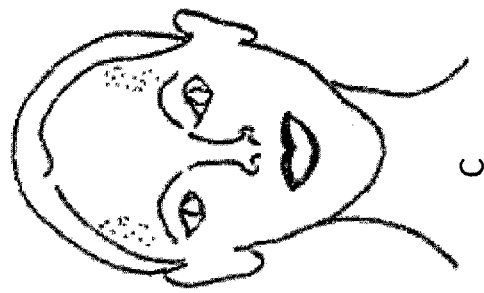
Figure 3:
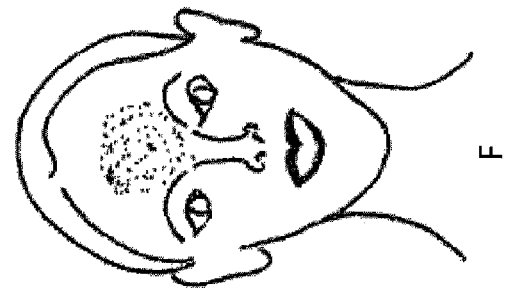

FIG. 3 shows nominal patterns of open pore cluster locations on the face for 5 different emotions. Face A is the baseline showing no emotion. Face B shows low level anxiety. Face C shows fear. Face D shows planned lying. Face E shows embarrassment and Face F, anger.

Upon observing the pores on individuals undergoing a variety of emotions during interviews or discussions, the location and duration of the pore opening varied with the emotion experienced by the individual. For example, as disclosed in Face B of FIG. 3, a low level of anxiety is apparent in the pores from a line of pores along the eyebrow ridge, inclusion between the eyebrows. As described in Face C of FIG. 3, the emotion of fear is signaled by pores opening along the temples. In many cases, where a topic is brought up during an interview, such as dogs, a person who has been bitten by a dog years ago, may have a reaction such as this along the temples, while at the same time rationalizing this fear with words, such as "Dogs are okay, they're very intelligent," the pores on the temples tend to show a type of "blinking" as the person has fear and then rationalizes it, thus having what might be termed a "tentative," "ambivalent," or "rationalized" fear reaction.

With respect to Face D, if a person has a planned lie, there may be large pores that remain persistently open for the duration of the interview positioned in a type of line that has a single or a few pores in the upper part of the central area of the forehead or slightly off to one side and that has some on the noise and one to a few pores along the line, all presenting an appearance similar to the stars of the handle of the Big Dipper on a clear night. Embarrassment, as shown in Face E, is apparent by open pores more widespread over the face whereas the desire not to speak about a topic may appear as pores around the mouth.

Conversely, a persistent pore opening is also telling as to the intensity or longstanding nature of the emotion. In the example above, for instance, the rationalization of a fear of dogs may be observed as the pores opening only moderately and then closing and opening in a manner that appears tentative or ambivalent. However, in other cases, when a topic is being discussed about which the person has very strong and deep feelings, a few pores may open very wide and stay open, even as the topic of the interview changes, indicating that the feeling generated in the person may be longstanding. Along with duration of pore opening, specific facial geographic patterns that can be identified as described in FIG. 3 have been related to experiencing some emotions, such as fear, anger, embarrassment (shame), or a planned lie.

Figure 4:
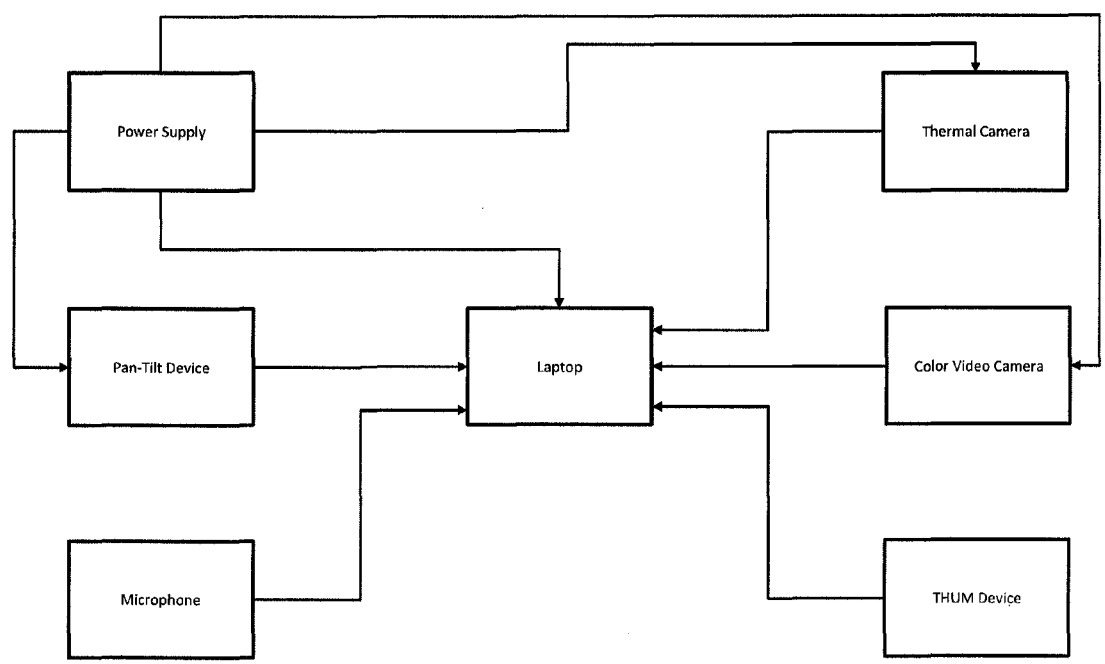
FIG. 4 shows a control system for operating the invention.

FIG. 4 shows a control system according to the present invention, including a laptop computer connected to a thermal camera, a color video camera, a microphone, a THUM (temperature and humidity) device, a power supply and a pan/tilt device.

Figure 5:
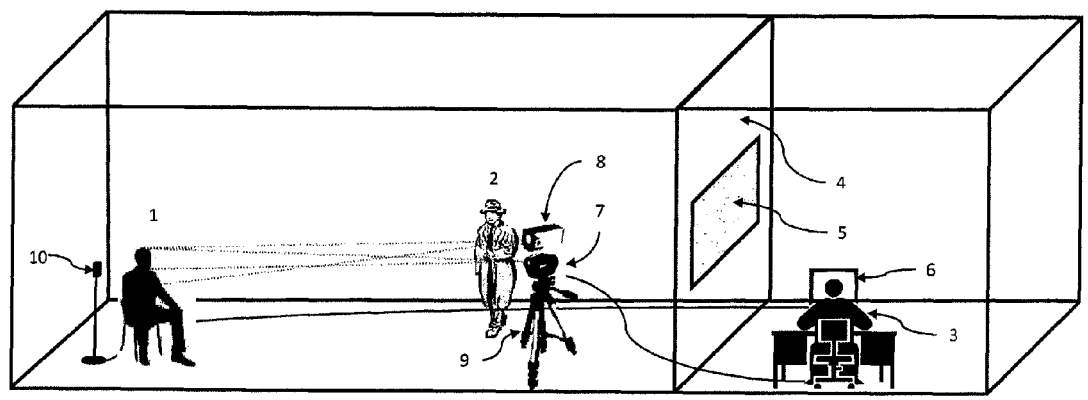
FIG. 5 shows an arrangement of the invention where the interviewee is looking at the video and thermal cameras.

FIG. 5 shows one embodiment of the invention in operation. The interviewee 1 is seated in a non-rolling chair and facing the thermal imager 7 and video camera 8 mounted on a tripod 9 or comparable mount located nearby. The interviewer 2 should be facing the interviewee and positioned such that the thermal camera 7 is behind the interviewer so that the focus of the interviewee 1 is on the interviewer 2 allowing full visibility of the interviewee's face by the thermal imager 7. In addition, there is a temperature and humidity device 10 located near the interviewee 1. As described in FIG. 5, an operator 3 is positioned behind a divider wall 4 having a 2-way mirror 5 and viewing a TV monitor or electronic display device 6 connected to laptop computer. A means of communication can be established between the interviewer 2 and the operator 3, preferably one not observable by the interviewee 1.

Figure 6:
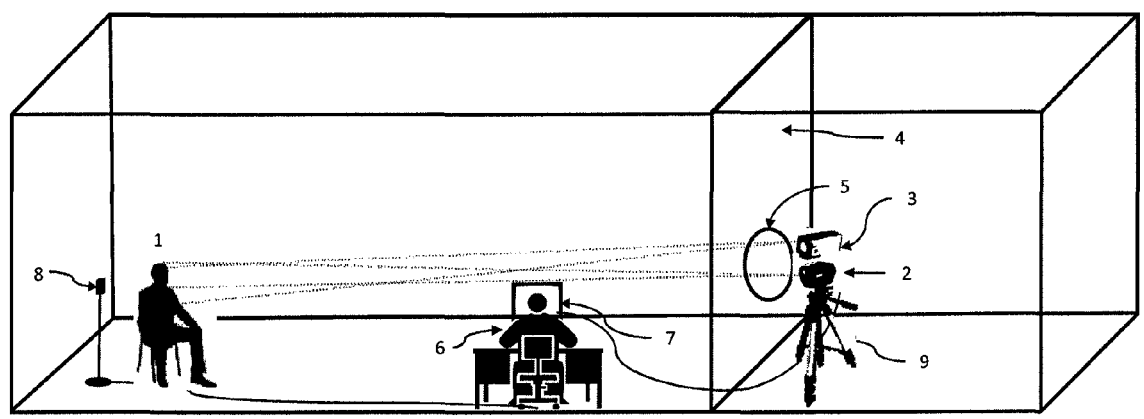
FIG. 6 shows another arrangement of the invention where the interviewee is not aware there is a video and thermal camera.

FIG. 6 shows another arrangement of the invention where the interviewer 6 and the operator are the same person and the interviewee 1 is not aware there is a thermal and video cameras focused on him or her (2, 3). The cameras are located behind a wall 4 and focused through a peep hole 5 in the wall. The peep hole 5 is covered by a sheet of germanium or plastic material transparent to mid- or long range radiation. The interviewer 6 and interviewee 1 are located in front of the wall 4. The interviewer has controls to operate the cameras 2, 3 and a TV monitor or electronic display device 7 all connected to a computer.

Figure 7:
FIG. 7 is a thermal image of the sweat pores in the face of an interviewee in the normal state.
Figure 8:
FIG. 8 is a thermal image of the sweat pores in the face of an interviewee in the open state.

FIGS. 7 and 8 are thermograms of the interviewee's face before and after being asked questions. In FIG. 7, the interviewee is calm and the pores remain closed. In FIG. 8, the interviewee immediately reacts to one or more questions and the open pores are visible in the thermal image. The small blotchy black dots seen on the forehead are the pores. Therefore, through the use of a thermal camera, the open pores are used as a gauge for activity in autonomic nervous system and provide a technique for detecting anxiety and/or stress.

These thermograms were of the forehead of the interviewee because it is the flattest part of the face and thus reduced the need for much depth of field of the camera configuration. Additionally, the forehead provides a great number of potential pores and appears highly sensitive to emotions. Furthermore, the forehead tends to be visible in many circumstances, not being covered by clothing or eyeglasses. There are disadvantages, however, to using only the forehead. Some people, for instance, have long bangs on the forehead. Others tend to have more active pores on their nose, cheeks, chin, or around the mouth, Therefore, the best instantiation of the camera for the invention should have enough resolution to visualize and observe pore activity on the whole face.

In order to allow an operator to concentrate on the subject of the interview, rather than viewing a screen or electronic display or TV monitor to make a discrimination of the general number of pores opening or closing, an automatic counting of the pores and their topographical locations can be applied to the invention. The automatic counting can be accomplished with an algorithm using the peak amplitude of the pore count after the question or stimulus as the measure of pore response. A threshold value is determined by the scenario, for example, a rise of 0.4 times the baseline value, defined as the number of pores open immediately before the question is asked or the stimulus presented. The responses to the questions or the stimulus that exceed the threshold proportion of open pores above the baseline at the peak response is used to determine if the person had a stress response. The pores are counted before and after each question for about 20 seconds. This includes a peak response, i.e., the ratio of the maximum number of open pores within 20 seconds after the question divided by the baseline number of open pores. The maximum number of pores that opens in response to a question typically occur rapidly between 5 and 7 seconds after the question has been asked. Another characteristic of a stress response to a question is that the pore count will have two peaks, a first peak response occurring between 5-7 seconds after the question and then another peak response, usually smaller than the first occurring about 12-15 seconds after the first response. This is a typical signature of a stress response to a relevant question, i.e., one that has a perceived risk for the interviewee.

The number of open pores at any particular time may be a response to many kinds of stimuli and their temporal patterns. The stimulus can be provided by questions, pictures, photographs and video or audio recordings, which are believed to contain relevance to the individual being tested. In general, in order to analyze the pores, there must be a period during which the subject is at a calm state or a relatively calm state so that the response to the stimulus and/or questions can be observed in the pore count. During the calm state, there may be very few or no visible open pores. In this case, when a stimulus is presented that causes any kind of tension, which can include general nervous tension related to the questioning itself by any authority figure, there will be an increase in the number of pores open. Even the sound of the interviewer's voice or his or her walking into the room can increase the open pores on the face. This increase in the number of open pores due to questioning can be separated from the pore response due to the relevance of a particular question by ensuring that there is a stability in the pore count before the question begins. This can easily be seen by the interviewer if he or she is observing thermal video on the display or if the pores are being counted automatically in real time and the interviewer can see or be told that the subject is at a baseline. This procedure is similar to that used in between questions during a polygraph examination. Usually, a time period of about one minute without any stimulus intervenes between each question with the polygraph.

The baseline state of the individual's pores can be related to a number of factors. Individuals vary in their response magnitudes and in their tendency to experience this response. In particular, the ambient temperature changes a person's pore responses to questioning. If the environment is cool, i.e., below 72 degrees Fahrenheit, the person will likely have less open pores as a baseline, and will require more nervous system responses to open pores. This is due to the fact that the body may be well below the threshold for sweating. In contrast, as the ambient temperature increases, the person is on the threshold of sweating and just a small amount of threat response can cause the pores to open to cool the body.

One stimulus used to obtain a response was for the interviewer to ask questions or mention certain topics, some of which may be benign to the subject and some of which may have relevance to topics that the subject does not wish to discuss. For example, in interviewing someone who may know about terrorist activities, or may be planning to perform some such malicious act, topics that reference certain terrorists or locations may cause the subject to experience temporary stress and lead to opening of the pores. Those topics that do not have this type of relationship to terrorist or malicious acts may not cause pores to open because the subject does not have a stress reaction to those benign topics. Thus, the interviewer can distinguish between those topics about which the subject has knowledge or information that he or she does not wish to reveal.

Questions such as: "Do you build bombs in your basement?" would have only a minimal stress effect on most people, the stress only due to their wondering why they would be asked such a question. However, the builder of bombs, who is very concerned about being discovered, would be expected to have a response well above threshold to any authority asking such a question. They may fear that their nefarious activity has been discovered or is in the process of being ferreted out.

In some cases, people who have been taking drugs that depress the central nervous system would have less than the expected response to questioning. This would be part of a threshold concept as well, since there is an expected small rise in pore count with questioning for innocent subjects. Data has shown that there is a significant population of bad actors having a below-normal responsiveness, who would fall under the low threshold and should be subsequently questioned further on those topics.

The determination of a stress response may be done after the fact for analysis of an interview or in real time. The interviewer may be able to watch the display as he or she is interviewing the subject and thereby can get immediate visual responses either by "eye-balling" the changes in the pore count or by a graphical output of the pore count. Another possibility is for the interviewer to be in the room with the subject and for another individual to be with the computer analysis in a separate room. The results of the automatic counting may then be displayed to the interviewer in any number of ways. For example, in real time a green/yellow/red light may be illuminated on some electronic device in the interviewer's field of view to indicate the emotional salience of the real time topic for the subject. The interviewer might also leave the interview room briefly and go to the analysis area to receive information on those topics about which the subject had a stress response. The automatic counting can be combined with other physiological responses such as breathing rate changes and eye blinks, which are also key physiological readings of the polygraph because they change when a subject is experiencing a psychological/emotional reaction to a particular topic. The electro-dermal activity, which is that measured by the pore count, accounts for about 60% of the information from a polygraph. The breathing rate accounts for another 25% of the information from a polygraph, so the combination of these two measures could provide a remote, non-contact polygraph including 85% of the information. This invention, however, provides much more information than from the polygraph since it includes details about the particular emotion whereas the polygraph produces only a line on a graph for each physiological measure. See FIG. 3.

One embodiment of the invention includes a thermal camera and an electronic display capable of showing the opening and closing of pores in response to a stimulus. It may also include a video camera to focus on and record the pores in the face of a person being tested. It may also include a laptop computer with a temperature and humidity sensor. Further, the invention may include a microphone to amplify questions which may be asked by an interviewer of the person. The microphone may be connected to the laptop. All these items are connected as described in FIG. 4.

Other instantiations would have the interviewee standing in front of a guard for primary screening to determine if that person should pass into an event. The use of pores to determine whether an individual is planning to cause a disturbance at an event has been tested with about 200 subjects and shown to be over 70% effective in detecting those with malicious intent and discriminating those who do not have malicious intent in such a primary screening situation. With an automatic face-detection algorithm steering the tripod 9 on which is mounted the cameras 7 and 8 as described in FIGS. 5 and 6, it is possible to view people of interest and observe the changes in the number of open pores.

One embodiment of the invention is the Remote Electrodermal Detection—FLIR Assessing Guilt or Red-FLAG. This system is used to determine if a person being interviewed is concealing information or feeling stressed by a particular discussion topic. If a particular topic is causing the person to be distressed, then follow-up questions are asked to try to identify the reason for the stress. The stress reaction is determined by observing the number of sweat pores on the face of the person being tested, which rapidly open in response to a specific question or topic. The pores are viewed by a thermal and color video cameras focused on the face of the person and located nearby but may be hidden from the person. The cameras are positioned on a pan-tilt tripod and operated through a computer, which is connected to a temperature and humidity device and a microphone. The opening of the pores are seen on an electronic display of the computer and recorded with the interview of the person on the hard drive of the computer.

The particular thermal camera used was a FUR Silver thermal camera with a Mid-Wave Indium Antimondide having a spectral range of 3-5 μm. A plug and play interface was provided that used a GigE interface for camera control and video transmission. The camera included a 27 mm lens although there was an optional telephoto lens of 100 mm.

Fingers, like the face, have many skin pores that open and close in response to stimuli and so the invention can be practiced by focusing a thermal camera on a finger, including thumb, of an individual being exposed to various stimuli.

The invention may be used in procedures similar to those used for a polygraph to determine whether a subject is having a stress reaction to a particular topic or question or whether the subject is afraid of getting caught in a lie or in revealing self-incriminating information to authorities.

Many soldiers returning from battle experience stress disorders. This invention can also be used to observe the stress reactions to topics of discussions, pictures, or videos for evaluation of stress disorders related to "fitness for duty," need for therapeutic intervention, and/or for the effectiveness of therapies. Observation of a recently returned soldier from Iraq showed that when the words "safety," "Baghdad," "friends," or "bomb" were used in conversation, hundreds of pores in the skin of the face immediately opened as observed through a thermal camera.

Similarly, the invention may also be used for evaluation of other types of psychological conditions such as t phobias. It may be useful in anger management classes and biofeedback therapies.

The invention includes the capability to obtain and measure other components of the polygraph without contact with the subject, but rather through the passive use of the thermal images. These other components include the respiration and blink timing, which both change in response to the "fight or flight" reaction. These physiological reactions can be seen with the invention and therefore provide cues as to the status of the nervous system from which is inferred that a person is experiencing a threat to his or her well-being.

Unlike the polygraph procedure, the invention does not require that the subject look at a point on the wall and keep his or her limbs still. When using the invention, the only requirement is that the face be in the field of view of the thermal camera. This is easily accomplished by having the camera behind the interviewer, either imbedded in the wall or on a tripod or gantry. When the subject looks at the interviewer, the face will be in the field of view.

The invention also provides something more than the polygraph. In many instances, it can provide information as to the nature of the emotion that is being experienced by the subject through the location pattern of clusters of open pores on the face and through whether the pores are "blinking" or more or less permanently open. For example, general nervous tension ordinarily experienced when people are undergoing interviews to assess their credibility shows up as a cluster of open pores along the plane of the eyebrows and just above them.

Additionally, as explained before, the invention can be used to parse the face into the regions corresponding to the different emotions using an automatic algorithm that creates a mask covering the area along the line of the eyebrows and just above, for example, to confirm an anxiety response as in general nervous tension. Also, the areas along the temples can be segmented by a mask and the pores counted in that region to indicate a fear response is taking place. This type of pore counting taking into consideration the general location of the pores can be accomplished by image processing software to obtain clues as to the specific emotion being experienced.

The invention has been described in an illustrative manner. It is to be understood that the terminology which has been used is intended to be in the nature of words of description, rather than limitation. For example, any thermal imager or IR sensor can be used in this invention instead of the thermal camera. Many modifications and variations of the invention are possible in light of the above teachings. Therefore, within the scope of the appended claims, the invention may be practiced other than as specifically described.

I claim:

1. A method for a rapid and passive identification of changes in a number of open sweat pores in the skin of an individual, comprising:
disposing a thermal camera at a predetermined location;
focusing the thermal camera on at least a portion of a predetermined skin surface of the individual so as to provide a thermal image without contacting the individual;
displaying the thermal image to enable real time viewing of the sweat pores on the portion of the predetermined skin surface;
visually identifying a baseline number of open sweat pores imaged on the thermal image of the portion of the predetermined skin surface prior to a stimulus;
interviewing the individual by presenting a stimulus;
visually identifying an opening of sweat pores imaged on the thermal image of the portion of the predetermined skin surface in response to the stimulus, wherein said response is a stress response characterized by a first maximal peak response followed by a second peak response;
numerically counting the identified opening of sweat pores imaged on the thermal image for about 20 seconds following the stimulus to compute a threshold determination of stress response, wherein an event marker is provided to selectively identify the imaged opening of sweat pores; and
determining a threshold stress response based on the numerical count of the identified opening of sweat pores exceeding the baseline number of open sweat pores by a margin of 40 percent.

2. The method of claim 1 wherein the thermal camera is disposed at a predetermined location so that the thermal camera is hidden from a view of the individual.

3. The method of claim 1 wherein the predetermined skin surface is a portion of a face.

4. The method of claim 1 wherein the stimulus is selected from a group consisting of one or more questions, pictures, video or audio recordings to be presented to the individual.

5. The method of claim 1 wherein the stimulus is a series of questions being asked to the individual.

6. The method of claim 1 further comprising providing a computer with an electronic display and a storage medium and coupling the thermal camera to the computer.

7. The method of claim 6 wherein displaying the thermal image comprises displaying the thermal image on the computer's electronic display.

8. The method of claim 6 wherein the computer is a laptop.

9. The method of claim 6 further comprising providing a temperature and humidity sensing device to enable monitoring of a temperature and humidity in a vicinity of the individual and coupling the sensing device to the computer.

10. The method of claim 6 further comprising providing a microphone to enable recording an audio during the step of interviewing and coupling the microphone to the computer.

11. The method of claim 6 further comprising providing a color video camera to enable recording a video during the step of interviewing and coupling the color video camera to the computer.

12. The method of claim 6 wherein the thermal camera is a forward looking infrared midrange camera.

13. The method of claim 6 further comprising providing an application program code disposed on the storage medium of the computer, said application program code is operable to enable recording on the storage medium of thermal images, a video and an audio during the step of interviewing.

14. The method of claim 13 wherein said application program code is operable to enable selectively providing said event marker at a selected location of the recording to identify the occurrence of the opening of the pores.

15. The method of claim 6 comprising providing an application program code disposed on the storage medium of the computer, said application program code is operable to enable selectively configuring the operation of the thermal camera.

16. The method of claim 6 comprising providing an application program code disposed on the storage medium of the computer, said application program code is operable to enable selectively configuring the operation of the video camera.

17. The method of claim 6 comprising providing an application program code disposed on the storage medium of the computer, said application program code is operable to enable selectively configuring the operation of the microphone.

18. A method for a rapid and passive determination of whether an individual is withholding information comprising:
providing a thermal camera to thermal image a face of the individual for visual detection of open sweat pores on the imaged face of the individual;
visually identifying a baseline number of open sweat pores imaged on the thermal image prior to interacting with the individual for about 20 seconds, wherein said response is a stress response characterized by a first maximal peak response followed by a second peak response;
requesting the individual to supply information;
observing the increase of open sweat pores in the skin of that individual in response to the request for information for about 20 seconds;
numerically counting the increased open sweat pores observed in the skin, wherein an event marker is provided to selectively identify the observed increase in the numeric count of open sweat pores; and
determining a threshold stress response based on the numerical count of the increased open sweat pores exceeding the baseline number of open sweat pores by 0.4 times the baseline number.

* * * * *